United States Patent [19]

Edward et al.

[11] 4,312,221

[45] Jan. 26, 1982

[54] HARDNESS TESTER MOUNTING APPARATUS

[76] Inventors: John C. Edward, 780 Callaway, Beaumont, Tex. 77706; Robert M. Edward, Jr., 18 Kittiwake Ct., The Woodlands, Tex. 77380

[21] Appl. No.: 144,530

[22] Filed: Apr. 28, 1980

Related U.S. Application Data

[63] Continuation-in-part of Ser. No. 944,548, Sep. 21, 1978, Pat. No. 4,199,976.

[51] Int. Cl.³ .............................................. G01N 3/40
[52] U.S. Cl. ............................................ 73/81; 73/83
[58] Field of Search ......................... 73/81, 82, 83, 12

[56] References Cited

U.S. PATENT DOCUMENTS

| | | | |
|---|---|---|---|
| 1,874,842 | 8/1932 | Abrahamson | 73/81 |
| 2,422,634 | 6/1947 | Riepert et al. | 73/81 |
| 3,732,727 | 5/1973 | Hinnergardt et al. | 73/81 |

*Primary Examiner*—James J. Gill
*Attorney, Agent, or Firm*—Bill B. Berryhill

[57] ABSTRACT

Mounting apparatus for use with a hardness tester which includes a reciprocating penetrator for measuring hardness properties of the materials to be tested. The mounting apparatus may comprise: an elongated base member having parallel upper and lower flat surfaces and provided with a hole substantially midway between the ends thereof; substantially parallel elongated shoe members attached to the base member adjacent its lower surface for contact with the material to be tested; and components for removably attaching the hardness tester to the base member so that its penetrator is disposed in the base member hole for reciprocal movement therein.

9 Claims, 2 Drawing Figures

HARDNESS TESTER MOUNTING APPARATUS

CROSS-REFERENCE TO RELATED APPLICATIONS

The present application is a continuation-in-part of copending patent application Ser. No. 944,548, filed Sept. 21, 1978 and entitled "Hardness Testing Apparatus", now U.S. Pat. No. 4,199,976.

BACKGROUND OF THE INVENTION

1. Field of the Invention

The present invention pertains to apparatus for testing properties of materials. In particular, it pertains to apparatus for testing the hardness properties of materials. More specifically, the present invention pertains to mounting apparatus suitable for mounting hardness testers for measuring hardness properties of large flat pieces of non-ferrous materials.

2. Brief Description of the Prior Art

It is frequently necessary to determine certain physical properties and characteristics of materials. This is particularly true in the production of metal goods where a range of properties, such as hardness may be specified or required in the production or fabrication thereof. Hardness, as generally applied to physical properties of materials such as metals, can be measured by determining resistance to penetration. Several scales or standards of reference for hardness of materials have been developed over the years. Two of the most common scales are the Rockwell and Brinell hardness scales.

Various testing methods have been developed to indicate or measure the hardness properties of materials. These hardness testing methods usually measure indentation or penetration of a penetrating device to which predetermined loads are applied. Commonly, the penetrating device, upon clamping of the material to be tested adjacent the tester, is placed against the material with a minor or preliminary load supplied thereto. Then a full or major load is applied to the penetrator. The difference of penetration of material between the minor and major load is measured on a suitable indicator. This measurement then gives an indication of the hardness of the material.

With many testers of the prior art, it is necessary to bring the material being tested to the tester or a work table for clamping therein prior to the test. This is sometimes difficult or impossible depending upon the shape of the material being tested. For example, a large flat plate is difficult to place in a relatively smaller clamping device. In testing tubular goods, clamping may result in inaccurate readings due to deformation of the tested goods.

Because of the problems associated with bringing certain goods to a tester or properly clamping the goods next to the tester, mobile testing apparatus have been developed. Mobile testers may be designed for clamping to the material being tested without the necessity of a permanent or stationary work table. In the previously identified co-pending patent application Serial No. 944,548, a mobile tester is provided with an electromagnet for magnetically attaching the testing apparatus to the material to be tested. Thus, a clamping assembly is not required. This solves the clamping problem in any applications in which the material being tested is ferrous. However, magnetic attachment cannot be used on non-ferrous materials, such as aluminum.

SUMMARY OF THE INVENTION

In the present invention, mounting apparatus is provided by which a hardness tester can be used to test the hardness properties of non-ferrous as well as ferrous materials, without the use of a clamping device. Mounting of the hardness tester is accomplished strictly by weight.

The mounting apparatus of the present invention may include an elongated base member of substantial weight having parallel upper and lower flat surfaces, the edges of which are joined by first and second side surfaces and the ends of which are joined by first and second end surfaces. Substantially parallel elongated shoe members may be attached to the base member adjacent its lower surface and near the edges thereof for contact with the material to be tested. A hole is provided through the base member substantially midway between its first and second end surfaces and having an axis which is substantially perpendicular to the upper and lower surfaces of the base member.

The hardness tester is attached to the base member by a mounting assembly which is very similar to the mounting assembly by which the hardness tester is attached to the electromagnetic clamping assembly disclosed in the aforementioned patent application Ser. No. 944,548. The weight of the base member should be sufficient to overcome the forces placed on the hardness tester penetrator in the major load position. If the weight of the base member is not great enough, an elongated weight increasing member may be selectively surmounted on the base member and/or first and second weight members of substantially equal weight may be removably surmounted on each end of the base member.

Thus, with the mounting apparatus of the present invention, a hardness tester can be used in testing materials without clamping the material in place. The weight of the mounting apparatus is such that the hardness tester can be placed directly on the material being tested whether it is ferrous or non-ferrous. This is particularly useful in testing large flat items such as aluminum plate or sheet materials.

Furthermore, the mounting apparatus is easily disassembled so that even though it is heavy when assembled, it can be easily moved in components. The hardness tester itself is affixed to the mounting apparatus in such a way that it can be easily removed for repair, maintenance or movement to another location. The mounting apparatus is extremely simple to manufacture and maintain. Other objects and advantages of the invention will become apparent from reading the specification which follows in conjunction with the accompanying drawings.

DESCRIPTION OF THE PREFERRED EMBODIMENT

Figure 2:
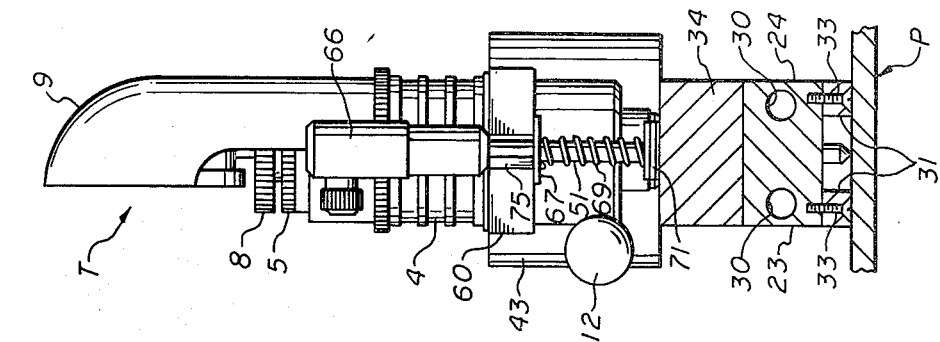
FIG. 2 is an end elevation view of the hardness tester of FIG. 1.
Figure 1:
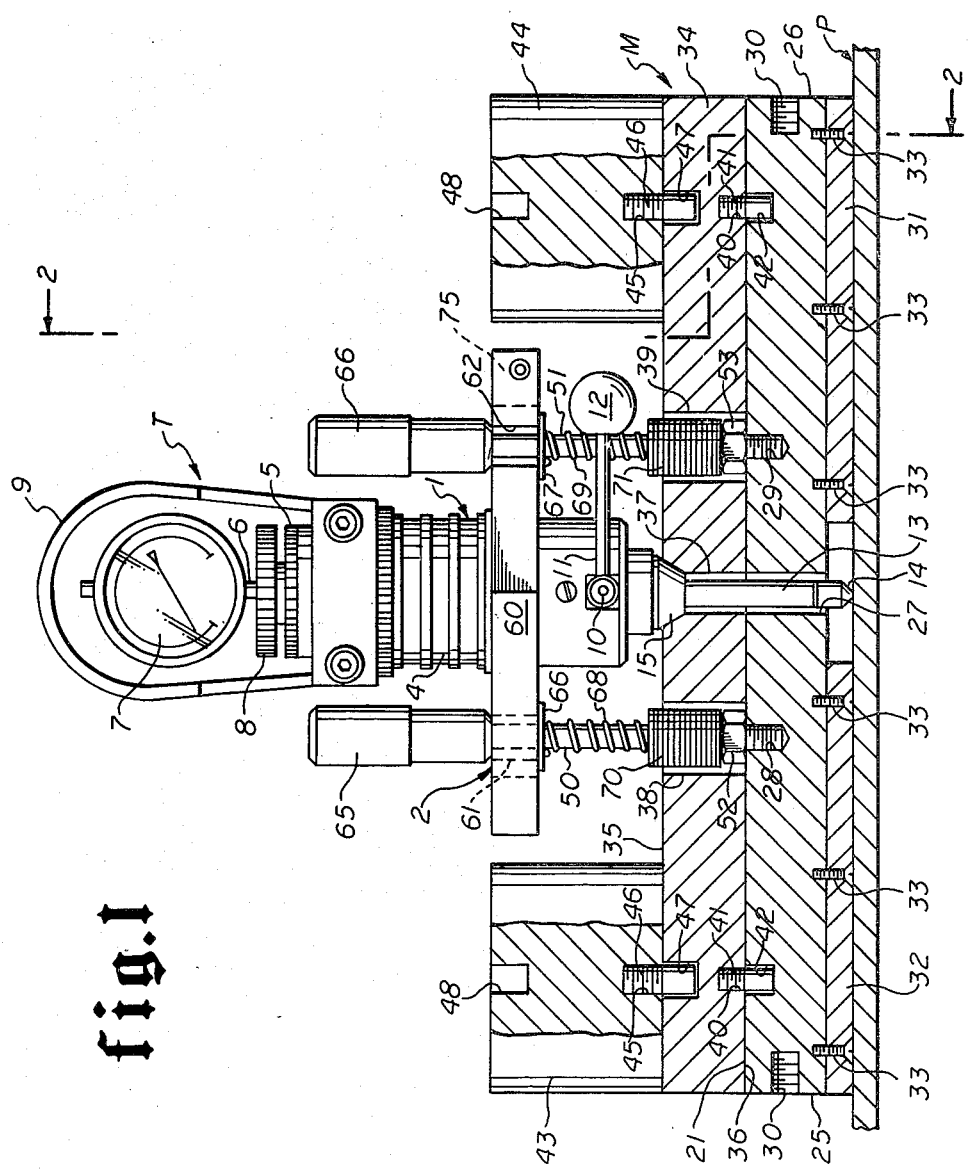
FIG. 1 is a side elevation view, partially in section, illustrating a hardness tester attached to mounting apparatus according to a preferred embodiment of the invention for measuring hardness properties of material.

Referring now to FIGS. 1 and 2, a Rockwell hardness tester T is shown in combination with mounting apparatus M for measuring the hardness of a piece of flat material or plate P. The tester includes a head assembly 1 and an attachment assembly 2 by which the tester T is removably attached to the mounting apparatus M.

The head assembly 1 comprises a cylindrical housing 4 in which may be contained a conventional load cell (not shown). The load cell is retained in the cylindrical housing 4 at its upper end by a threaded cap 5 having a central opening therethrough (not shown) in which is disposed the stem 6 of a dial gauge 7. The stem 6 of the dial gauge 7 may be rigidly clamped in this disposition in any suitable manner. As illustrated, it is held by a wedge or collet device (not shown) maintained by a locknut 8. A protective cage or cover 9 may be provided for protecting the dial gauge 7.

At the base of cylindrical housing 4 is an operating cam 10 to which is attached an operating handle and knob 11 and 12, respectively, the purpose of which will be more fully understood hereafter. The design of the operating cam 10 and the details thereof will not be explicitly described. It is sufficient to note that the cam 10 extends through the lower end of the cylindrical housing 4 in the manner of a shaft for selective contact with the lower end of load cell assembly contained in housing 4 and through a plunger member (not shown) to which an extension 13 and penetrator 14 is attached at the lower end thereof. A threaded cap 15 may be provided for replacing the extension 13 and penetrator 14 as will be more fully described hereafter.

The mounting apparatus M of the present invention includes an elongated base member 20 having parallel upper and lower flat surfaces 21 and 22, respectively, the edges of which are joined by first and second side surfaces 23, 24; and the ends of which are joined by first and second end surfaces 25, 26. A hole 27 is provided through the base member 20 substantially midway between the first and second end surfaces 25 and 26 and the axis of which is substantially perpendicular to the upper and lower surfaces 22, 21. The base member 20 may be provided with a pair of threaded holes 28 and 29 on opposite sides of the hole 27. The ends of the base member 20 may also be provided with threaded holes 30 which may be fitted with threaded members (not shown) by which the base member 20 and other components of the mounting apparatus M may be lifted or handled. The base member 20 is relatively heavy and may be made of steel, cast iron or any other relatively heavy material.

Attached to the base member 20, adjacent the lower surface 22 and near the edges thereof are two pairs of elongated shoe members 31 and 32. Although two pairs are shown, one pair extending the entire length of the base member 20 could also be used. The shoe members 31 and 32 may be attached by screws 33 which pass through holes provided in the shoe members 31, 32 for engagement with corresponding threadedly tapped holes in base member 20. The shoe members 31 and 32 contact the plate P being tested for hardness and support the entire weight of the mounting apparatus M and the tester T.

Although the base member 20 is relatively heavy, there may be times when more weight is needed for the mounting apparatus M. In such cases, an elongated weight increasing member 34 may be selectively surmounted on top of the base member 20. The weight increasing member 34 includes parallel upper and lower flat surfaces 35, 36 and has a first hole 37 substantially midway between the ends thereof corresponding with the first hole 27 in the base member 20. Second and third holes 38 and 39, on opposite sides of the first hole 37, are provided in coaxial alignment with the threadedly tapped holes 28, 29 in the base member 20. However, they are of larger diameter so as to allow the disposition of a nut member or washer therein as will be more fully understood hereafter. To assure proper registration of the weight increasing member 34 with base member 20, threadedly tapped holes 40 and correspondingly threaded pins 41 may be provided at the lower surface of the weight increasing member 34. Corresponding holes 42 are provided in the upper surface of base member 20 for registrable engagement by the downwardly depending ends of the pins 41.

There may be occasions when even more weight will be required. On such occasions, first and second weight members 43 and 44, of substantially equal weight, may be removably surmounted on each end of the weight increasing member 34 or, if the weight increasing member 34 is not used, directly on the ends of base member 20. Although the weight members 43 and 44 may be of any shape, they are shown as being cylindrical and having at the lower ends thereof threadedly tapped holes 45 for threaded engagement by a correspondingly threaded pin 46. Corresponding holes 47 are provided in the upper surface of the weight increasing member 34 so that the weight members 43 and 44 may be placed for proper weight distribution and registration relative to the base member 20. If the weight increasing member 34 is not in place, the holes 42 in the base member 20 may be used for such registration.

The attachment assembly 2 by which the hardness tester T is removably attached to the mounting apparatus M includes first and second stud members 50 and 51 threadedly engaging the threaded holes 28 and 29 of the base member 20 for projection upwardly from the upper surface of the base member 20 on opposite sides of hole 27 and hole 37, if the weight increasing member 34 is being utilized. In fact, the axes of the stud members 50 and 51 are parallel to the axis of holes 27 and 37. Lock nuts 52 and 53 assure that the studs 50 and 51 remain securely in place.

The attachment assembly 2 also includes a frame or yoke 60 which is attached to the cylindrical housing 4 of the tester T. The frame 60 is provided with holes 61 and 62 for receiving the upper end of studs 50 and 51. Threadedly attached to the upper ends of studs 50 and 51 above the frame 60 are increased diameter nuts 65 and 66 which may be machined or adapted for hand manipulation. The lower ends of the nuts 65 and 66 may be slightly tapered but provide downwardly facing shoulders for resting against the frame 60. Disposed beneath the frame 60 are washers 66 and 67 and helical springs 68 and 69. Other washers 70 and 71 may be provided at the base of the springs 68 and 69. It will be noted that the holes 61 and 62 in the frame 60 open toward opposite sides of the frame 60 so that by slight rotation of the tester T and the frame 60, in a counterclockwise direction, the holes 61 and 62 will disengage the studs 50 and 51 for removal of the tester assembly T from the mounting apparatus M.

In operation, the mounting apparatus M would be placed on the plate P or other material to be tested so that the shoes 31 and 32 rest thereon. Depending upon the type of tester T and the magnitude of the forces to be applied against the penetrator 14, the weight increasing member 34 and/or the weight members 43 and 44 would be surmounted on the base member 20. The tester assembly T would be placed in the position shown in FIGS. 1 and 2 by engagement of the holes 61 and 62 of the frame 60 with the stud members 50 and 51. It will be noted that the extension member 13 and penetrator 14 are disposed within holes 27 and 37 (if the weight increasing member 34 is in place). Then the hand-manipulated nuts 65 and 66 would be rotated until the tester assembly T is in the no load position. Next, the operating handle 11 is moved ninety degrees to the minor load position, causing a predetermined minor load force to be applied against the penetrator 14 engaging the plate P. A minor load reading or zeroing of the gauge 7 is accomplished at this point. Then the handle 11 is moved to the major load position (one hundred eighty degrees from the position shown in FIG. 1) in which a predetermined major load is transferred to the penetrator 14 through the shaft 13. The amount of penetration is indicated on the gauge 7 and from the gauge reading, the hardness of the plate P can be determined.

As can be understood from the previous description, the mounting apparatus M may comprise any combination of the base member 20, the weight increasing member 34 and the weight members 43 and 44. In fact, additional weight members can be surmounted on the weight members 43 and 44. For this reason, the weight members 43 and 44 may also be provided with upper holes 48 for engagement by corresponding registration pins of additional weight members. The components of the mounting apparatus M are easily separable and removable. Thus, they can be handled individually rather than having to handle the total weight of the mounting assembly M. In addition, as already seen, the tester assembly T is removably attached by the frame 60 and studs 50 and 51 so that the tester assembly T can be separately handled. This makes the entire assembly much more portable and easy to transfer from one piece of work to another or from one testing location to another.

Thus, the mounting apparatus of the present invention allows hardness testing of materials, such as plate P, which are not easily placed on a work table or in a clamping assembly as is needed with hardness testers of the prior art. The holding of the tester against the material to be tested is completely by weight and is especially useful for testing materials which are non-ferrous and incapable of being tested by electromagnetic clamped testers, such as the one described in the aforementioned copending patent application Ser. No. 944,548. The components are easy to manufacture, assemble, disassemble, maintain and transport.

While a single embodiment of the invention has been described herein, many variations thereof can be made without departing from the spirit of the invention. For example, instead of simply mounting the weight increasing member 34 and/or weight members 43, 44 on base member 20 by registration pins 41, 46, through holes may be provided in these members 34, 43, 44 and bolts inserted for threaded engagement with corresponding threaded holes in base member 20 (where holes 42 are shown). In this manner the entire assembly is fastened together and if desired a lifting handle can be attached to the bolts so that the entire tester and mounting apparatus may be lifted by overhead lifting equipment. In fact, it is intended that the scope of the invention be limited only by the claims which follow.

We claim:

1. Mounting apparatus for use with a hardness tester of the type having a housing in which is carried a reciprocating penetrator for measuring hardness properties of materials to be tested, said mounting apparatus comprising:
    an elongated base member having parallel upper and lower flat surfaces, the edges of which are joined by first and second side surfaces and the ends of which are joined by first and second end surfaces, a hole being provided through said base member substantially midway between said first and second end surfaces and the axis of which is substantially perpendicular to said upper and lower surface;
    substantially parallel elongated shoe members attached to said base member adjacent said lower surface and near the edges thereof for contact with said material to be tested; and
    means for removably attaching said hardness tester housing to said base member so that said penetrator is disposed in said base member hole for reciprocal movement therein and for engagement with said material to be tested.

2. Hardness tester mounting apparatus as set forth in claim 1 including first and second weight members of substantially equal weight removably surmounted on each end of said base member.

3. Hardness tester mounting apparatus as set forth in claim 2 in which said first and second weight members are cylindrical and at least one end of which is provided with a coaxial hole for engagement with a corresponding pin member also engaging corresponding holes in said base member.

4. Hardness tester mounting apparatus as set forth in claim 1 in which said means for attaching said hardness tester to said base member comprises first and second stud members projecting upwardly from said upper surface of said base member on opposite sides of said hole therethrough and the axes of which are parallel to said hole axis, the housing of said hardness tester being attached to a frame member having holes at each end thereof for receiving the upper ends of said first and second stud members and by which said hardness tester is removably attached to said base member.

5. Hardness tester mounting apparatus as set forth in claim 4 in which one of said frame holes opens toward one side of said frame and the other hole opens toward the opposite side of said frame so that upon slight rotation of said frame member about the axis of said base member hole, said studs are disengageable from said holes for removal of said tester from said base member.

6. Hardness tester mounting apparatus as set forth in claim 5 in which the upper end of said stud members are provided with increased diameter portions, the diameter of which is greater than the diameter of said frame member holes, spring members being disposed about said studs between said base member and said frame member, biasing said frame against said increased diameter portions of said stud members.

7. Hardness tester mounting apparatus as set forth in claim 4 including an elongated weight increasing member having parallel upper and lower flat surfaces, a first hole substantially midway between the ends thereof, second and third holes on opposite sides of said first hole corresponding with said first and second stud members allowing said weight increasing member to be selectively surmounted on said base member, its lower surface engaging the upper surface of said base member and said stud members projecting through said second and third holes, said first hole being in coaxial registration with said base member hole.

8. Hardness tester mounting apparatus as set forth in claim 7 including first and second weight members of substantially equal weight removably surmounted on each end of said elongated weight increasing member.

9. Hardness tester mounting apparatus as set forth in claim 8 in which at least one end of each of said first and second weight members and both ends of said weight increasing member are provided with holes for corresponding engagement by pin members for proper weight distribution and registration of said first and second weight members relative to said base member and said weight increasing member.

* * * * *